United States Patent [19]

Baniel et al.

[11] Patent Number: 4,994,609

[45] Date of Patent: Feb. 19, 1991

[54] PRODUCTION OF CITRIC ACID

[75] Inventors: Avraham M. Baniel, Jerusalem; David Gonen, Haifa, both of Israel

[73] Assignee: Innova S.A., Luxembourg, Luxembourg

[21] Appl. No.: 534,635

[22] Filed: Jun. 6, 1990

[51] Int. Cl.$^5$ ................... C07C 51/48; C07C 59/265
[52] U.S. Cl. ..................... 562/580; 562/584
[58] Field of Search ............................. 562/580, 584

[56] References Cited

U.S. PATENT DOCUMENTS

| | | | |
|---|---|---|---|
| 4,251,671 | 2/1981 | Allen | 562/584 |
| 4,310,691 | 1/1982 | Bengtsson | 562/584 |
| 4,334,095 | 6/1982 | Baniel | 562/584 |
| 4,720,579 | 1/1988 | Kulprathipanja | 562/584 |

Primary Examiner—Paul J. Killos
Attorney, Agent, or Firm—Helegott & Karas

[57] ABSTRACT

Recovery of citric acid from a citric acid fermentation broth.

The process comprises
(i) Subjecting said citric acid fermentation broth to evaporation to produce a concentrate with a citric acid concentration of at least 80% of the saturation value at the evaporation temperature;
(ii) subjecting such concentrate to an extraction operation with a recycled amine extractant citric acid solution in which the citric acid concentration is below the equilibrium value which corresponds to the broth concentrate at the extraction temperature, to produce a more concentrated amine extractant citric acid solution and aqueous citric acid raffinate;
(iii) withdrawing the aqeuous extraction raffinate from said extraction operation, bleeding off a small fraction thereof and recycling the balance to the said evaporation;
(iv) withdrawing the said concentrated amine extractant citric acid solution extract and back-extracting it with water to obtain an aqueous citric acid solution and a depleted amine extractant citric acid solution the concentration of which is below the equilibrium value which corresponds to the broth concentrate; and
(v) recycling said depleted amine extractant citric acid solution to the extraction operation.

3 Claims, 2 Drawing Sheets 4,994,609

PRODUCTION OF CITRIC ACID

FIELD OF THE INVENTION

The present invention is in the field of citric acid production and is directed to a new process for the recovery of citric acid values from citric acid fermentation broths by solvent extraction.

BACKGROUND OF THE INVENTION AND PRIOR ART

Citric acid is produced commercially by fermentation of certain organic substrates. The most common substrate for such fermentation are carbohydrates such as dextrose and sucrose, but it is also possible to use straight-chain hydrocarbons. Citric acid fermentation produces a so-called fermentation broth from which citric acid values are recovered in form of citric acid or citrates.

In certain industrial operations a virtually pure substrate of the kind specified is used to which only the necessary nutrients have to be added. In such an operation the recovery of clean citric acid or citrate by solvent extraction is relatively easy.

In other operations impure substrates such as molasses are used for the fermentation. Such impure substrates contain high percentages of organics that are not carbohydrates as well as various electrolytes. In such operations the resulting fermentation broth contains a substantial amount of impurities and the recovery of clean citric acid or citrate by solvent extraction is more complicated and impractical in practice.

U.S. Pat. No. 4,275,234 describes a solvent extraction process for recovering citric acid from broths obtained from the fermentation of pure substrates. In the performance of this process a water-immiscible organic extractant is used which comprises at least one secondary or tertiary amine in which the total number of carbon atoms per molecule is at least 20, dissolved in a water-immiscible, organic, non-polar or polar solvent, and the operation involves extraction of the broth with such an extractant at a low temperature and back extraction of the extract with water at a higher temperature. While this process provides for high recoveries of citric acid, it entails high costs. One source of the cost is the need to cool large volumes of fermentation broth and of solvent for extraction and to reheat solvent and heat water for back-extraction.

A further source of costs of the process according to U.S. Pat. No. 4,275,234 is the need to dispose of the aqueous extraction residue (broth raffinate) which contains substantially all of the water of the extracted fermentation broth and various, mainly organic substances such as residual carbohydrates, amino compounds, etc. Such disposal can be effected by evaporation of the bulk of the water and using the remaining concentrate, e.g. as cattle feed. Such commercialisation does, however, not compensate for the significant evaporation cost.

Alternatively, the aqueous extraction residue obtained in the process of U.S. Pat. No. 4,275,234 may be subjected to biological effluent treatment, but this again is cost intensive regardless of whether it is done at the citric acid plant itself or shipped to an outside sewage treatment system.

U.S. Pat. No. 4,334,095 describes a multi-stage total extraction process by which a citric acid fermentation broth is extracted with a mixture of a water-immiscible amine and a water-immiscible organic acid dissolved in a suitable water-immiscible solvent, and the resulting extract is back-extracted with water. This process is, however, impractical and capital intensive.

It is the object of the present invention to provide an alternative simple process for the recovery of pure citric acid from a citric acid fermentation broth derived from fermentation of a pure substrate such as described above.

SUMMARY OF THE INVENTION

In the following description and claims a water-immiscible organic extractant comprising at least one secondary or tertiary amine in which the total number of carbon atoms in molecule is at least 20, dissolved in a water-immiscible, organic, non-polar or polar solvent will be referred to as "amine extractant".

In accordance with the invention there is provided a process for the recovery of citric acid from a citric acid fermentation broth comprising (i) Subjecting said citric acid fermentation broth to evaporation to produce a concentrate with a citric acid concentration of at least 80% of the saturation value at the evaporation temperature;

(ii) subjecting such concentrate to an extraction operation with a recycled amine extractant citric acid solution in which the citric acid concentration is below the equilibrium value which corresponds to the broth concentrate at the extraction temperature, to produce a more concentrated amine extractant citric acid solution and an aqueous citric acid raffinate;

(iii) withdrawing the aqueous extraction raffinate from said extraction operation, bleeding off a small fraction thereof and recycling the balance to the said evaporation;

(iv) withdrawing the said concentrated amine extractant citric acid solution extract and back-extracting it with water to obtain an aqueous citric acid solution and a depleted amine extractant citric acid solution the concentration of which is below the equilibrium value which corresponds to the broth concentrate; and (v) recycling said depleted amine extractant citric acid solution to the extraction operation.

Thus in the process according to the present invention the only waste product is the fraction of the aqueous extraction raffinate which is bled-off. If desired, the citric acid in this bleed may be used for the production of alkali metal or ammonium citrates in accordance with the process of U.S. Pat. No. 3,944,606 which comprises extraction with an amine extractant and back-extraction with a compound that forms an alkali metal or ammonium salt of citric acid.

Alternatively, the bled-off raffinate may be shipped to a citric acid plant in which a fermentation broth is treated by the so-called "lime/sulphuric acid process". In such a process the fermentation broth is first subjected to so-called "liming", i.e. treatment with calcium hydroxide, the resulting calcium citrate is filtered off, washed, decomposed with aqueous sulphuric acid, the calcium sulphate that forms is filtered off and the resulting aqueous acid solution is gradually evaporated in a crystallizer whereupon citric acid crystallizes. The lime/sulphuric acid process is eminently suitable and is the only one used for recovering citric acid from fermentation broths derived from impure substrates such as molasses. Many plants use both molasses and pure carbohydrates without deriving advantages from the purity of the latter. By adjoining the new process to treat broths derived from the pure substrate and sending the bleed to the lime/sulphuric acid unit, optimisation for economic effectiveness becomes possible.

By employing either of these methods for the treatment of the bleed solution a nearly 100% recovery of citric acid values from the fermentation broth is achieved.

Alternatively, the bled-off raffinate may be used as is as animal feed additive.

It should be noted that in accordance with the invention the bled-off raffinate is a small fraction of the total raffinate holding, as a rule no more than 10% of the citric acid fed into the operation and consequently whatever the nature of the treatment to which the bled-off raffinate is subjected, only relatively small volumes have to be handled.

It is thus seen that in accordance with the present invention the recovery of citric acid from a concentrated fermentation broth involves small volumetric throughputs and accordingly requires relatively small size equipment. Also no heating or cooling is required to control the solvent extraction and all this provides for inherently low investment and low operational costs. Moreover, as the process does not generate waste products a new plant can be established in locations where the strictest rules obtain with respect of safeguarding the environment. For the same reasons the process is ideal for expanding production of existing lime/sulphuric acid plants not permitted to increase their output of waste gypsum.

DESCRIPTION OF THE DRAWINGS

For better understanding the invention will now be described, by way of example only, with reference to the annexed drawings without being limited thereto. In the drawings.

DESCRIPTION OF SPECIFIC EMBODIMENTS

Figure 1:
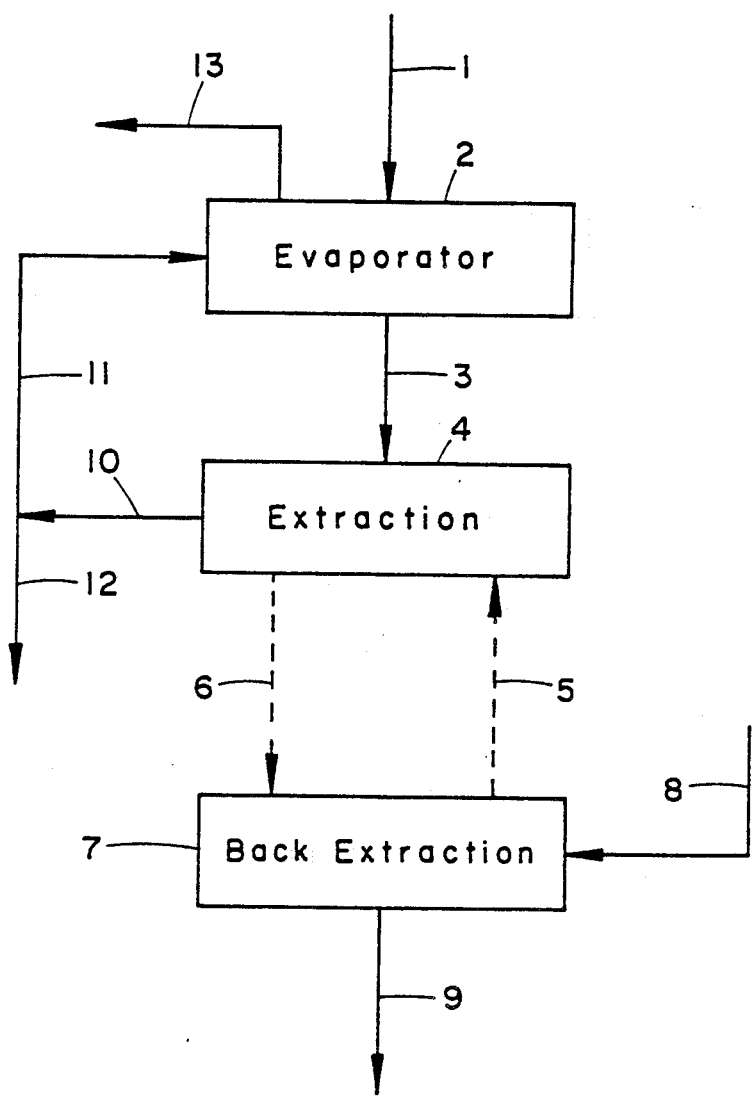
FIG. 1 is a flow sheet of one embodiment of the process according to the invention.

In the embodiment of FIG. 1 a clarified fermentation broth is fed at 1 into an evaporator 2 and concentrated broth is withdrawn at 3 and charged into an extractor 4 where it is contacted with an amine extractant citric acid solution arriving at 5, whose concentration is below the equilibrium value of the system concentrated broth/amine extractant. In consequence the amine extractant is loaded with more citric acid to yield a concentrated amine extractant solution which is withdrawn at 6 and fed into an extractor 7 where it is back-extracted with water arriving at 8. An aqueous citric acid solution is withdrawn from extractor 7 at 9.

From extractor 4 an aqueous raffinate is withdrawn at 10, the bulk of which is recycled at 11 to evaporator 2 while a small fraction is withdrawn at 12 as bleed.

Vapour resulting from the evaporation in evaporator 2 is vented at 13.

It is thus seen that in addition to the product aqueous citric acid solution withdrawn at 9, the process also yields a raffinate containing all the impurities originally present in the fermentation broth as the only waste product. This product can be used as is as animal feed or else processed for the recovery of further citric acid values either in accordance with the teachings of U.S. Pat. No. 3,944,606 or by charging it into a lime/sulphuric acid operation as specified.

Figure 2:
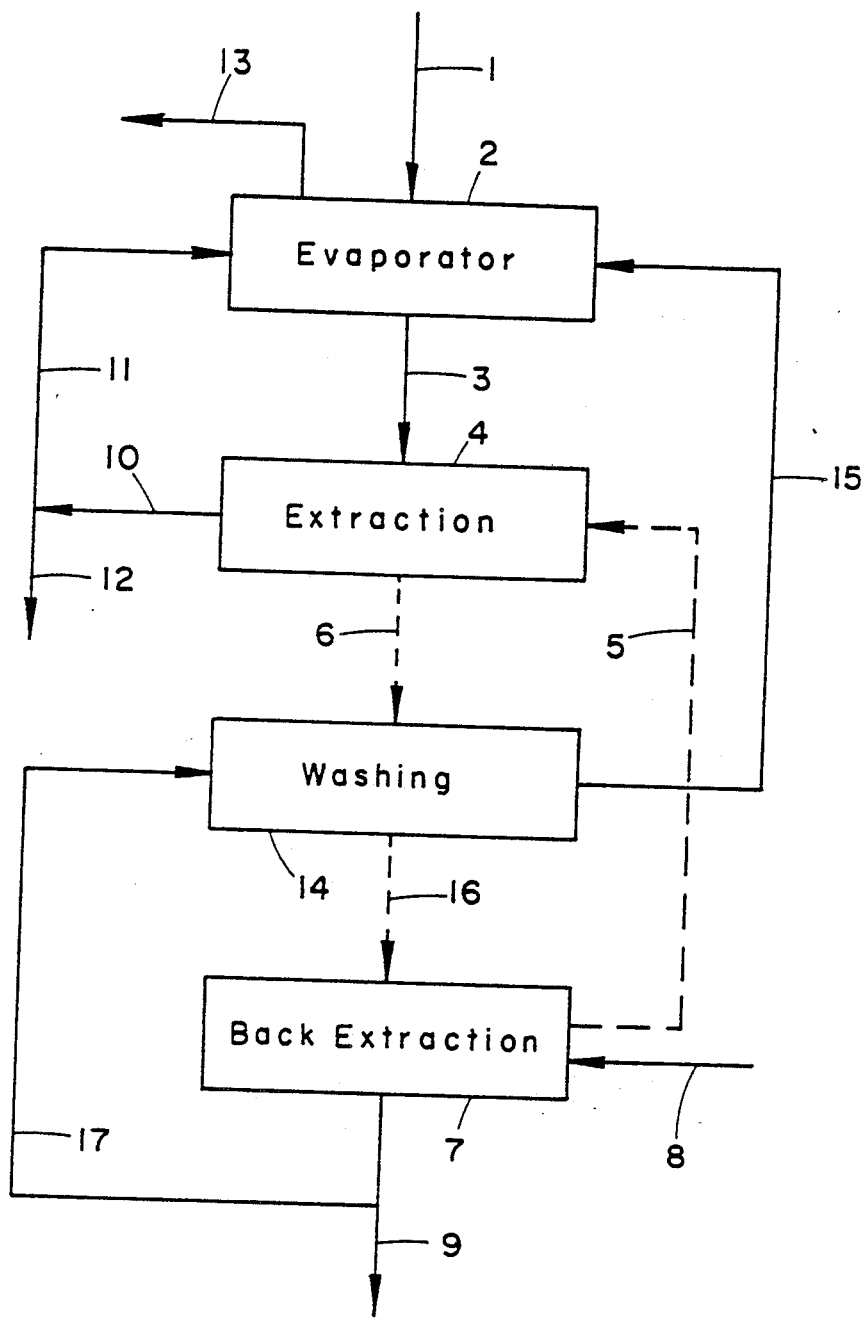
FIG. 2 is a flow sheet of another embodiment.

The embodiment of the process according to the invention shown in FIG. 2 is basically similar to that of FIG. 1 and similar flow lines and unit operations are indicated by the same reference numerals.

In addition to the unit operations in FIG. 1, the embodiment of FIG. 2 comprises a contactor unit 14 in which the citric acid solution withdrawn at 6 from extractor 4 is subjected to an intermediary washing with recycled citric acid solution fed into contactor 14 at 17 and the resulting aqueous extract is recycled at 15 to evaporator 2. The washed amine extractant citric acid solution is withdrawn from contactor 14 at 16 and charged into the extractor 7 for back-extraction with water as specified with reference to FIG. 1. A fraction of the product aqueous citric acid solution withdrawn at 9 is recycled at 17 to the intermediary washing operation in the washing contactor 14 while the broth is withdrawn as a product.

As a result of the washing operation in contactor 14 most of the impurities together with a small proportion of the citric acid are removed and returned to evaporator 2. For the rest, the operation is similar to that of the embodiment of FIG. 1.

The product aqueous citric acid solution withdrawn at 9 in both embodiments of FIGS. 1 and 2 may, if desired, be treated with active charcoal to remove traces of solvents and any other impurities. It may be used as such, be concentrated and sold as concentrated solution or the water may be completely evaporated to dryness in order &o obtain solid, crystalline citric acid. All this is known per se and need not be further described.

It has surprisingly been found that in the performance of the process according to the invention it is possible to allow the impurities to build up in the evaporator 2 to a high level such that the fraction of raffinate withdrawn at 12 may be so dosed that no more than about 10% of the total citric acid fed into the process is withdrawn as waste while the remaining 90% are recovered in the process itself. As already mentioned, the bled-off 10% fraction of citric acid may, if desired, also be recovered as citric acid or salts, or alternatively be used as is as animal feed additive.

It is customary in citric acid manufacture to subject the fermentation broth to a preliminary purification by ion exchange or treatment with active charcoal. If these conventional operations are applied to fermentation broths charged into the operation at 4 and/or to the concentrate withdrawn from evaporator 2 at 3, the amount of raffinate bled off at 12 can be reduced so as to account only for 5% or even less of the total citric acid fed into the extraction operation.

From the foregoing it is evident that the process according to the invention is environment-friendly.

The following example further illustrates the invention.

EXAMPLE

The operation was in accordance with the flow sheet of FIG. 2, with the evaporation temperature in concentrator 2 being within the range of 68°–70° C. The temperature throughout the system was maintained above 65° C. by proper insulation of all lines and unit operations and the temperature of the water introduced at 8 into the back-extraction operation was above 50° C.

The Table below refers to 100 units of citric acid in fermentation broth 1. Streams are characterised by total weight and citric acid content. Solvent extraction operations are characterised by the number of transfer stages; the equipment is not specified since all three of the most common equipment types—mixer-settlers, columns, centrifuges—are suitable. Solvent composition in grs/Kg of composition: tridodecylamine 530; n-octanol 63; isoparaffinic diluent 407.

In this example 90% of the citric acid in the broth are recovered as pure acid in stream 9 and 10% in the bleed 12. About 27% of the citric acid in the concentrated broth 3 are extracted per pass. The largest combined throughput is in extraction; in a plant recovering 10,000 metric tons per year it amounts to less than 40 tons/hr which is quite modest. As will be obvious to experts in the art of solvent extraction, this throughput can be further greatly reduced by increasing the number of stages.

TABLE

| No. in FIG. 2 | CA wt % | Total wt per 100 CA | Stages | Comments |
|---|---|---|---|---|
| 1 | 18 | 556 | — | broth |
| 2 | — | — | — | evaporation |
| 3 | 67 | 696 | — | concentrated broth |
| 4 | — | — | 2 | EXTRACTION |
| 5 | 12 | 2354 | — | depleted EXTRACTANT |
| 6 | 16 | 2465 | — | loaded EXTRACTANT |
| 7 | — | — | 4 | BACK-EXTRACTION |
| 8 | 0 | 67 | — | water |
| 9 | 52 | 169 | — | product |
| 10 | 63 | 547 | — | EXTRACTION aq. residue |
| 11 | 63 | 531 | — | recycle to Evaporator |
| 12 | 63 | 16 | — | bleed |
| 13 | 0 | 402 | — | water |
| 14 | — | — | 1 | WASHING |
| 15 | 52 | 170 | — | WASHING aq. residue |
| 16 | 16 | 2447 | — | washed loaded EXTRACTANT |
| 17 | 52 | — | 5 | product recycle |

We claim:
1. A process for the recovery of citric acid from a citric acid fermentation broth comprising
   (i) Subjecting said citric acid fermentation broth to evaporation to produce a concentrate with a citric acid concentration of at least 80% of the saturation value at the evaporation temperature;
   (ii) subjecting such concentrate to an extraction operation with a recycled amine extractant citric acid solution in which the citric acid concentration is below the equilibrium value which corresponds to the broth concentrate at the extraction temperature, to produce a more concentrated amine extractant citric acid solution and an aqueous citric acid raffinate;
   (iii) withdrawing the aqueous extraction raffinate from said extraction operation, bleeding off a small fraction thereof and recycling the balance to the said evaporation;
   (iv) withdrawing the said concentrated amine extractant citric acid solution extract and back-extracting it with water to obtain an aqueous citric acid solution and a depleted amine extractant citric acid solution the concentration of which is below the equilibrium value which corresponds to the broth concentrate; and
   (v) recycling said depleted amine extractant citric acid solution to the extraction operation.
2. A process according to claim 1 comprising subjecting the said concentrated amine extractant citric acid solution to washing with a small amount of water prior to the back-extraction, and recycling the wash water to the evaporation.
3. A process according to claim 1 comprising treating the product aqueous acidic acid solution with charcoal.

* * * * *